US011432852B1

(12) United States Patent
Melkent et al.

(10) Patent No.: US 11,432,852 B1
(45) Date of Patent: Sep. 6, 2022

(54) SCREW SHANK BASED TISSUE RETRACTION

(71) Applicant: Warsaw Orthopedic, Inc., Warsaw, IN (US)

(72) Inventors: Anthony J. Melkent, Germantown, TN (US); Cristian A. Capote, Memphis, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 0 days.

(21) Appl. No.: 17/208,590

(22) Filed: Mar. 22, 2021

(51) Int. Cl.
*A61B 17/70* (2006.01)
*A61B 17/02* (2006.01)

(52) U.S. Cl.
CPC ........ *A61B 17/7082* (2013.01); *A61B 17/025* (2013.01); *A61B 2017/0256* (2013.01)

(58) Field of Classification Search
CPC .... A61B 17/7074–7082; A61B 17/025; A61B 2017/0256
See application file for complete search history.

(56) References Cited

U.S. PATENT DOCUMENTS

| | | | |
|---|---|---|---|
| 2,370,407 | A | 2/1945 | McCartney |
| 4,438,769 | A | 3/1984 | Pratt et al. |
| 4,570,624 | A | 2/1986 | Wu |
| 4,763,548 | A | 8/1988 | Leibinger et al. |
| 4,887,020 | A | 12/1989 | Graham |
| 5,649,931 | A | 7/1997 | Bryant et al. |
| 5,667,513 | A | 9/1997 | Torrie et al. |
| 6,189,422 | B1 | 2/2001 | Stihl |
| 6,860,889 | B2 | 3/2005 | Bonati et al. |
| 6,945,933 | B2 | 9/2005 | Branch et al. |
| 7,011,658 | B2 | 3/2006 | Young |
| 7,090,680 | B2 | 8/2006 | Bonati et al. |
| 7,494,463 | B2 | 2/2009 | Nehls |
| 7,575,581 | B2 | 8/2009 | Lovell |
| 7,578,822 | B2 | 8/2009 | Rezach et al. |
| 7,618,424 | B2 | 11/2009 | Wilcox et al. |
| 7,854,751 | B2 | 12/2010 | Sicvol et al. |
| 7,976,463 | B2 | 7/2011 | Dewey et al. |
| 7,988,699 | B2 | 8/2011 | Martz et al. |
| 8,157,809 | B2 | 4/2012 | Butters et al. |

(Continued)

*Primary Examiner* — Eduardo C Robert
*Assistant Examiner* — Steven J Cotroneo
(74) *Attorney, Agent, or Firm* — Fox Rothschild LLP; P. Marshall Ticer (57) ABSTRACT

A surgical instrument configured to enable simultaneously driving a bone screw into a boney structure of a patient and delivering of a blade within the patient adjacent the bone screw is disclosed. The surgical instrument may include an elongated outer-sheath extending in a longitudinal direction from a proximal end to a distal end, for example. The elongated outer-sheath may include an interior cavity that defines a centrally disposed longitudinal axis that extends in the longitudinal direction, for example. The surgical tool may include a central-sheath disposed within the interior cavity that extends in the longitudinal direction, for example. The surgical instrument may further include an inner-shaft rotatably supported by the central-sheath that extends in the longitudinal direction, for example. The inner-shaft may include a driver configured to selectively drive a bone screw upon rotation of the inner-shaft about the longitudinal axis, for example.

17 Claims, 11 Drawing Sheets

(56) References Cited

U.S. PATENT DOCUMENTS

| | | |
|---|---|---|
| 8,162,952 B2 | 4/2012 | Cohen et al. |
| 8,172,750 B2 | 5/2012 | Miles et al. |
| 8,303,602 B2 | 11/2012 | Biedermann et al. |
| 8,317,692 B2 | 11/2012 | Loftus et al. |
| 8,357,184 B2 | 1/2013 | Woolley et al. |
| 8,435,269 B2 | 5/2013 | Woolley et al. |
| 8,439,832 B2 | 5/2013 | Miles et al. |
| 8,460,310 B2 | 6/2013 | Stern |
| 8,506,574 B2 | 8/2013 | Butters et al. |
| 8,535,320 B2 | 9/2013 | Woolley et al. |
| 8,562,521 B2 | 10/2013 | Miles et al. |
| 8,602,982 B2 | 12/2013 | Miles et al. |
| 8,608,746 B2 | 12/2013 | Kolb et al. |
| 8,636,655 B1 | 1/2014 | Childs |
| 8,747,307 B2 | 6/2014 | Miles et al. |
| 8,852,089 B2 | 10/2014 | Blackwell et al. |
| 8,876,869 B1 | 11/2014 | Schafer et al. |
| 8,894,573 B2 | 11/2014 | Loftus et al. |
| 8,915,925 B2 | 12/2014 | Butters et al. |
| 9,044,280 B1 | 6/2015 | Arambula et al. |
| 9,050,146 B2 | 6/2015 | Woolley et al. |
| 9,084,642 B2 | 7/2015 | Peultier |
| 9,101,413 B2 | 8/2015 | Masson et al. |
| 9,131,966 B2 | 9/2015 | Solitario, Jr. et al. |
| 9,149,308 B2 | 10/2015 | Biedermann et al. |
| 9,216,016 B2 | 12/2015 | Fiechter et al. |
| 9,301,743 B2 | 4/2016 | Miles et al. |
| 9,307,972 B2 | 4/2016 | Lovell et al. |
| 9,326,798 B2 | 5/2016 | Kolb et al. |
| 9,345,463 B2 | 5/2016 | Butters et al. |
| 9,414,828 B2 | 8/2016 | Abidin et al. |
| 9,510,874 B2 | 12/2016 | Kruger |
| 9,517,092 B2 | 12/2016 | Biedermann et al. |
| 9,532,814 B2 | 1/2017 | Harper |
| 9,572,605 B2 | 2/2017 | Shipp |
| 9,615,862 B1 | 4/2017 | Doubler et al. |
| 9,622,795 B2 * | 4/2017 | Reitblat ............. A61B 17/7079 |
| 9,700,293 B2 | 7/2017 | Cryder et al. |
| 9,795,370 B2 * | 10/2017 | O'Connell ......... A61B 17/0206 |
| 9,888,948 B2 | 2/2018 | Petit |
| 9,962,147 B2 | 5/2018 | O'Connell et al. |
| 9,968,385 B2 | 5/2018 | Biedermann |
| 10,039,539 B2 | 8/2018 | Friedrich et al. |
| 10,058,359 B2 | 8/2018 | Black et al. |
| 10,092,283 B2 | 10/2018 | Cryder et al. |
| 10,123,826 B2 | 11/2018 | Harper |
| 10,172,652 B2 | 1/2019 | Woolley et al. |
| 10,194,958 B2 | 2/2019 | Bobbitt et al. |
| 10,231,724 B1 | 3/2019 | Lovell et al. |
| 10,258,390 B2 * | 4/2019 | Biedermann ...... A61B 17/7082 |
| 10,278,687 B2 | 5/2019 | Cryder et al. |
| 10,278,786 B2 | 5/2019 | Friedrich et al. |
| 10,363,022 B2 | 7/2019 | Serokosz et al. |
| 10,390,862 B2 | 8/2019 | Bobbitt et al. |
| 10,405,842 B2 | 9/2019 | Kim |
| 10,426,454 B2 | 10/2019 | Ponmudi et al. |
| 10,470,752 B2 | 11/2019 | Butters et al. |
| 10,499,896 B2 | 12/2019 | Abidin et al. |
| 10,499,897 B2 | 12/2019 | Truckey |
| 10,507,046 B2 | 12/2019 | Reitblat et al. |
| 10,603,026 B2 | 3/2020 | Cryder et al. |
| 10,660,628 B2 | 5/2020 | O'Connell et al. |
| 10,660,631 B1 | 5/2020 | Boesel et al. |
| 2002/0020255 A1 | 2/2002 | Simon et al. |
| 2005/0203533 A1 | 9/2005 | Ferguson et al. |
| 2006/0069391 A1 * | 3/2006 | Jackson ............. A61B 17/7038 606/62 |
| 2007/0043378 A1 * | 2/2007 | Kumar ............... A61B 17/7082 606/104 |
| 2007/0083086 A1 * | 4/2007 | LeVahn ................. A61B 17/02 600/210 |
| 2010/0331849 A1 | 12/2010 | Riesinger et al. |
| 2011/0098537 A1 | 4/2011 | Justis et al. |
| 2011/0130793 A1 * | 6/2011 | Woolley ............. A61B 17/7076 606/279 |
| 2012/0296171 A1 * | 11/2012 | Lovell ................. A61B 17/0218 600/213 |
| 2013/0046147 A1 | 2/2013 | Nichter et al. |
| 2014/0024900 A1 | 1/2014 | Capote et al. |
| 2014/0031874 A1 | 1/2014 | Kucharzyk et al. |
| 2015/0257797 A1 * | 9/2015 | Biedermann ...... A61B 17/7082 606/305 |
| 2015/0282855 A1 * | 10/2015 | Bess .................. A61B 17/7082 606/86 A |
| 2015/0313585 A1 * | 11/2015 | Abidin ............... A61B 17/0206 600/213 |
| 2016/0296266 A1 * | 10/2016 | Chandanson ....... B25B 23/0035 |
| 2016/0345952 A1 | 12/2016 | Kucharzyk et al. |
| 2017/0049428 A1 * | 2/2017 | Cryder .................. A61B 17/708 |
| 2018/0035990 A1 | 2/2018 | Eftekhar |
| 2018/0153585 A1 | 6/2018 | Levine |
| 2018/0206833 A1 | 7/2018 | O'Connell et al. |
| 2018/0271507 A1 | 9/2018 | Gasser |
| 2019/0008498 A1 | 1/2019 | McClymont et al. |
| 2019/0029737 A1 * | 1/2019 | Wall ................... A61B 17/8886 |
| 2019/0216451 A1 | 7/2019 | Cryder et al. |
| 2019/0231334 A1 | 8/2019 | Serokosz et al. |
| 2019/0298327 A1 | 10/2019 | Serokosz et al. |
| 2019/0350572 A1 | 11/2019 | Ponmudi et al. |
| 2019/0388079 A1 | 12/2019 | Kim |
| 2020/0054361 A1 | 2/2020 | Peultier et al. |
| 2020/0093529 A1 | 3/2020 | Biedermann et al. |
| 2020/0113606 A1 | 4/2020 | Reitblat et al. |
| 2020/0113713 A1 | 4/2020 | LaMarca et al. |
| 2020/0121310 A1 | 4/2020 | Butters et al. |
| 2020/0245994 A1 | 8/2020 | O'Connell et al. |
| 2021/0059724 A1 * | 3/2021 | Rezach ............... A61B 17/7002 |
| 2021/0153915 A1 * | 5/2021 | Hyeon ................. A61B 17/861 |

* cited by examiner

SCREW SHANK BASED TISSUE RETRACTION

CROSS-REFERENCE TO RELATED APPLICATIONS

This application hereby incorporates by reference each of the following U.S. Patent Applications. U.S. Pat. No. 10,456,122, filed Mar. 13, 2013 and titled SURGICAL SYSTEM INCLUDING POWERED ROTARY-TYPE HANDPIECE; U.S. patent application Ser. No. 16/560,587, filed Sep. 4, 2019 and titled SURGICAL INSTRUMENT AND METHOD; U.S. patent application Ser. No. 14/645,232 filed Mar. 11, 2015, titled "SURGICAL INSTRUMENT AND METHOD" now U.S. Pat. No. 10,285,740 granted May 14, 2019; U.S. patent application Ser. No. 16/395,574, filed Apr. 26, 2019 and titled Surgical instrument and method; and U.S. patent application Ser. No. 17/166,265, filed Feb. 3, 2021 and titled "MODULAR SURGICAL INSTRUMENT SYSTEM AND METHOD FOR SHANK-BASED RETRACTION AND DISTRACTION."

FIELD

In one aspect, the present disclosure generally relates to medical devices and more particularly to a system and method for delivery of a blade and bone screw for retraction of patient tissue. In another aspect, the present disclosure is generally related to systems and methods using a modular retractor blade and various distractors and/or retractors to provide retraction and distraction for use in a mini-open transforaminal lumbar interbody fusion (TLIF) spine surgery. The associated systems and methods disclosed herein may be used for other surgeries and are not limited to the specific examples disclosed herein.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs, which include implants such as bone fasteners, connectors, plates and vertebral rods are often used to provide stability to a treated region. These implants can redirect stresses away from a damaged or defective region while healing takes place to restore proper alignment and generally support the vertebral members. Surgical instruments are employed, for example, to engage the fasteners for attachment to the exterior of two or more vertebral members.

Spinal disorders may result in pain, nerve damage, and loss of mobility. While, non-surgical treatments may be effective to treat some spine disorders, others will require surgical treatments, such as without limitation, spinal fusions. During, a mini-open transforaminal lumbar interbody fusion (TLIF) spine surgery, an incision can be made off the midline to access both disc space and pedicles. Other spine surgeries may place the incision in a different location. Various tools are used to perform retraction with blades to expose a portion of the spine or boney structures through the incision. Other instruments are used to perform distraction. The interchange of these different instruments may increase the length of time required to perform the surgery. This disclosure describes methods and systems directed to addressing the problems described above, and/or other issues.

SUMMARY

The techniques of this disclosure generally relate to, for example, a modular surgical instrument system for delivery of a modular retractor blade and a bone screw for use with various distractors to provide retraction and/or distraction of patient tissue. The systems and methods may be discussed in relation to, for example, in an open, mini-open transforaminal lumbar interbody fusion (TLIF) spine surgery, although they are of course equally applicable to any other surgical procedure in which it may be advantageous to deliver a retractor blade and a bone screw simultaneously.

Various embodiments in accordance with the principles of this disclosure describe a surgical instrument having an elongated outer-sheath extending in a longitudinal direction from a proximal end to a distal end, for example. The surgical instrument may include an elongated outer-sheath that has an interior cavity that defines a centrally disposed longitudinal axis that extends in the longitudinal direction, for example. The surgical tool may include a blade configured to couple to and uncouple from the elongated outer-sheath via a coupling portion. The surgical tool may include a central-sheath disposed within the interior cavity and extending in the longitudinal direction, for example. The surgical instrument may further include an inner-shaft rotatably supported by the central-sheath and that extends in the longitudinal direction, for example. The inner-shaft may include a driver disposed proximate the distal end, and the inner-shaft may be rotatable about the longitudinal axis. Additionally, in various embodiments, the surgical instrument may be configured to enable simultaneously driving the bone screw into a boney structure of a patient in an installed position and delivering of the blade within the patient adjacent the installed position, for example.

Various embodiments in accordance with the principles of this disclosure describe a surgical system. The surgical system may include a blade, a bone screw, and a surgical instrument, for example. The surgical instrument may be configured to enable simultaneously driving the bone screw into a boney structure of a patient in an installed position and delivering the blade within the patient adjacent the installed position, for example. In various embodiments, the surgical instrument may include an elongated outer-sheath extending in a longitudinal direction from a proximal end to a distal end, and the elongated outer-sheath may have an interior cavity defining a centrally disposed longitudinal axis extending in the longitudinal direction, for example. Additionally, the surgical instrument may include a rotatable driver disposed within the interior cavity and that extends in the longitudinal direction, for example. In various embodiments, the blade may be configured to selectively couple to and uncouple from the elongated outer-sheath, and directly contact a head portion of the bone screw while the surgical instrument drives the bone screw into the boney structure of the patient, for example.

Various embodiments describe a method for simultaneously delivering a blade and a bone screw. The method may include the step of providing a surgical instrument that includes an elongated outer-sheath extending in a longitudinal direction from a proximal end to a distal end, for example. The elongated outer-sheath may have an interior cavity defining a centrally disposed longitudinal axis extending in the longitudinal direction, and the elongated outer-sheath may have a coupling portion disposed proximate to the distal end, for example. The surgical tool may include a central-sheath disposed within the interior cavity and extending in the longitudinal direction and an inner-shaft rotatably supported by the central-sheath and extending in the longitudinal direction, for example. In various embodiments, the inner-shaft may also include a driver disposed proximate the distal end, for example. The method may further include the steps of providing a blade comprising a bone screw receiving portion and coupling the blade to the elongated outer-sheath via the coupling portion, for example. The method may further include the steps of providing a bone screw having a head portion generally corresponding in size and shape to the bone screw receiving portion, and coupling the bone screw to the driver, for example. The method may further include the steps of installing, simultaneously, the bone screw in a boney structure of a patient in an installed position and the blade in the patient, for example.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Embodiments of the present disclosure relate generally, for example, to spinal stabilization systems, and more particularly, to surgical instruments for use with spinal stabilization systems. Embodiments of the devices and methods are described below with reference to the Figures.

The following discussion omits or only briefly describes certain components, features and functionality related to spinal stabilization systems, which are apparent to those of ordinary skill in the art. It is noted that various embodiments are described in detail with reference to the drawings, in which like reference numerals represent like parts and assemblies throughout the several views, where possible. Reference to various embodiments does not limit the scope of the claims appended hereto because the embodiments are examples of the inventive concepts described herein. Additionally, any example(s) set forth in this specification are intended to be non-limiting and set forth some of the many possible embodiments applicable to the appended claims. Further, particular features described herein can be used in combination with other described features in each of the various possible combinations and permutations unless the context or other statements clearly indicate otherwise.

Terms such as "same," "equal," "planar," "coplanar," "parallel," "perpendicular," etc. as used herein are intended to encompass a meaning of exactly the same while also including variations that may occur, for example, due to manufacturing processes. The term "substantially" may be used herein to emphasize this meaning, particularly when the described embodiment has the same or nearly the same functionality or characteristic, unless the context or other statements clearly indicate otherwise.

Figure 1:
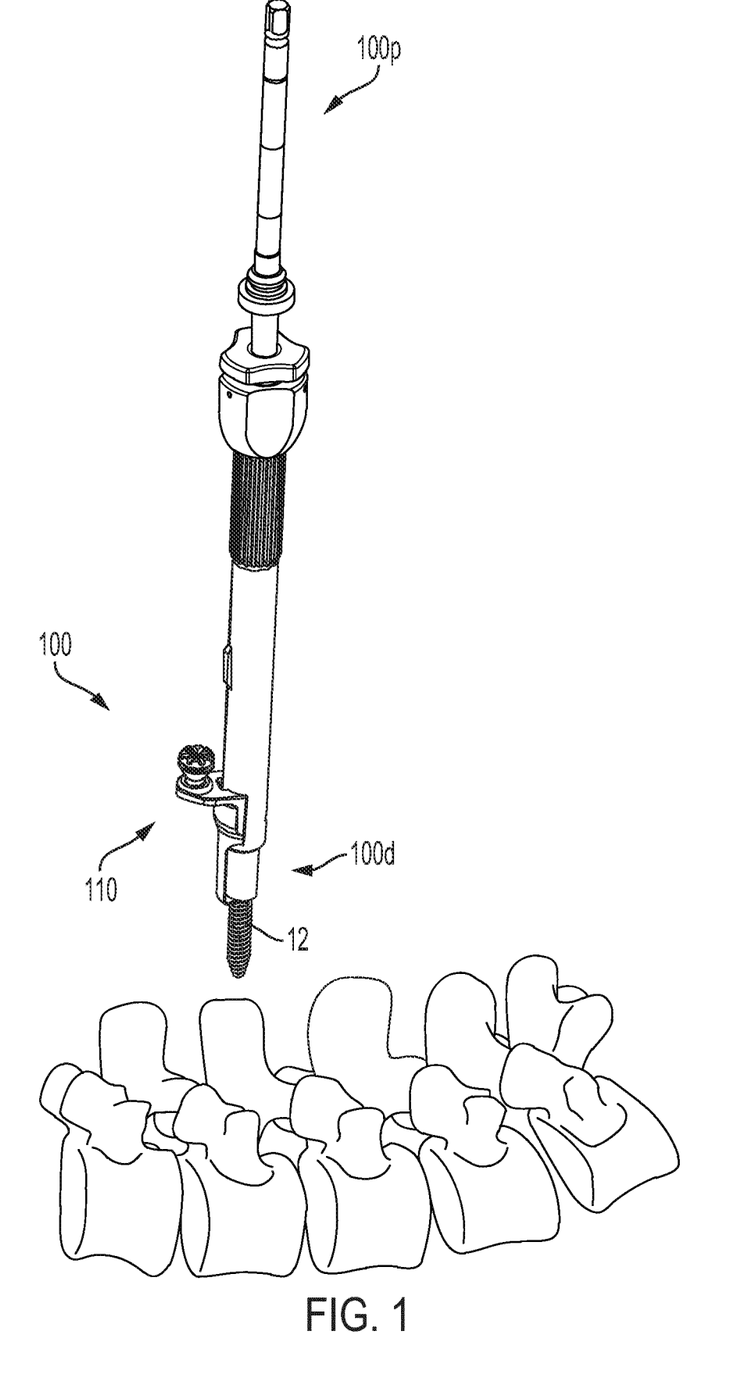
FIG. 1 is a perspective view of a surgical tool.
Figure 2:
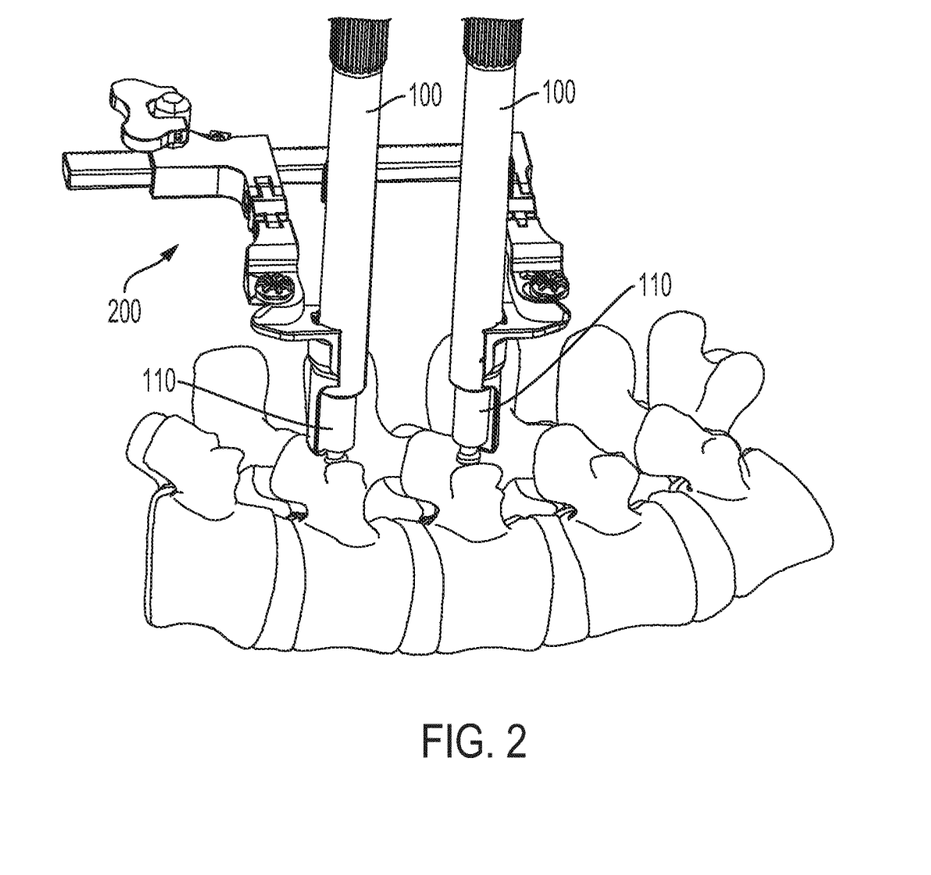
FIG. 2 is a perspective view of a retractor in use with the surgical tool of FIG. 1.

Referring generally to FIGS. 1-11 a surgical tool 100 is disclosed. Surgical tool 100 may be referred to as blade and screw delivery tool in some embodiments. For example, as illustrated in FIGS. 1 and 2, surgical tool 100 may concurrently deliver (i) a bone screw 12 or other anchoring member into a boney structure and (ii) a modular blade 110 for tissue retraction of surrounding soft tissue of a patient. Surgical tool 100 may include a proximal end 100p and a distal end 100d, for example. Surgical tool 100 may be coupled to a rotational drive instrument at the proximal end 100p and a bone screw 12 or other anchoring member may be coupled at the distal end 100d. At least one rotational drive instrument may be the POWEREASE™ System sold by Medtronic and/or the powered rotary-type handpiece described in U.S. Pat. No. 10,456,122, the disclosure of which is incorporated herein by reference in its entirety.

It shall be understood that in some embodiments and surgical procedures surgical tool 100 may be inserted through a previously established surgical path such as an incision in a patient to enable bone screw 12 to reach the target location. Various exterior and interior sheaths, shafts, and functional attributes of surgical tool 100 are disclosed in detail below.

As shown in FIG. 2, and in some surgical procedures, it may be advantageous to utilize two surgical tools 100 for securing a bone screw 12 into a superior vertebrae and an inferior vertebrae, for example. Concurrently with delivering bone screw 12 into the respective vertebrae, a respective blade 110 may also be delivered into an incision in the patient for preventing adjacent soft tissue form covering up bone screw 12 and/or subsequent retraction of surrounding soft tissue with a retractor, for example. Each blade 110 may be securely and removably coupled to a retractor 200 as will be explained in further detail below. It shall be understood that although retractor 200 is illustrated with only two blades 110, retractor 200 may be configured to couple to any number of blades 110 and manipulate blades 110 in any appropriate manner. For example, retractor 200 may articulate blades 110, move blades 110 upwards and downwards, move blades 110 side to side, and or couple to additional blades, shims, extension blades, etc. (not illustrated in FIG. 2).

Figure 3:
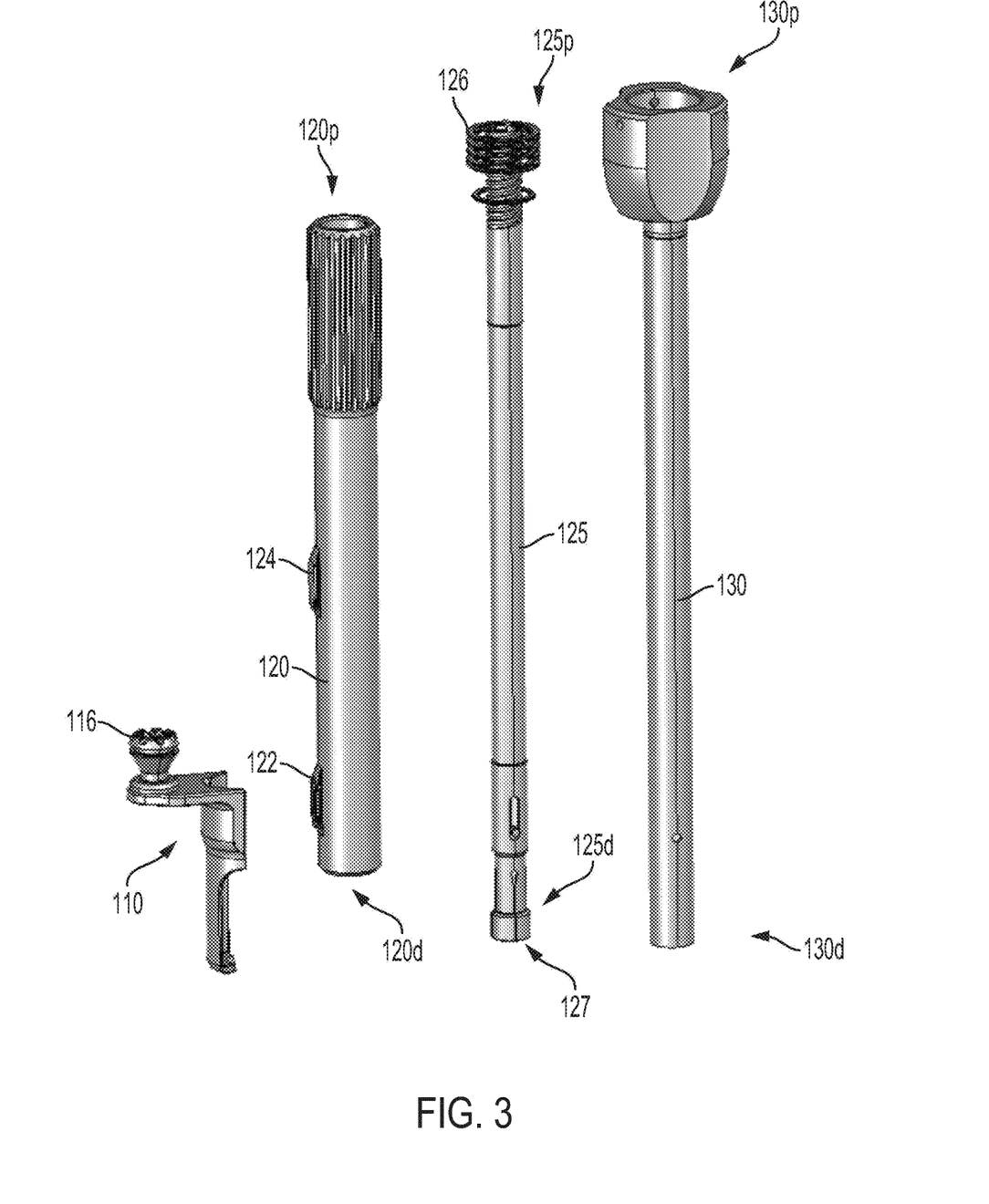
FIG. 3 is an exploded parts view of the surgical tool of FIG. 1.

FIG. 3 is an example exploded parts view of the surgical tool 100 and a modular blade 110. In the example illustration, surgical tool 100 may be composed of an outer-sheath 120 having a generally cylindrical shape and an open void space inside the interior of outer-sheath 120. Outer-sheath 120 may include various coupling portions such as lower coupling portion 122 and upper coupling portion 124, for example. Coupling portions 122 and 124 may be utilized to securely and removably connect with various blades 110 to outer-sheath 120, for example. Outer-sheath 120 may extend lengthwise in a longitudinal direction from a proximal end 120p to a distal end 120d and define a centrally disposed longitudinal axis projecting through the interior of outer-sheath 120 in a direction from the proximal end 120p to the distal end 120d, for example. The interior of outer-sheath 120 may comprise an inner diameter void space configured to house a tool for driving bone screw 112, for example. Central-sheath 130 may be disposed within the inner diameter portion (central void space) of outer-sheath 120, for example. In some embodiments, central-sheath 130 may be secured to outer-sheath 120 by pins, screws, locking channels, dovetail configuration, etc. In other embodiments, central-sheath 130 may be snug fit and not necessarily rigidly secured as explained in the immediately prior sentence. Central-sheath 130 may include a proximal end 130p and a distal end 130d. In use, when central-sheath 130 is nested in a coaxial relationship with outer-sheath 120 a portion of the proximal end 130p of central-sheath 130 may extend beyond a portion of the proximal end 120p of outer-sheath 120, for example. In various embodiments, the proximal end 130p of central-sheath 130 may be configured to couple to a drive instrument (not illustrated) and/or house a proximal end 125p of inner-shaft 125, for example.

In various embodiments, inner-shaft 125 may extend in a longitudinal direction from a proximal end 125p to a distal end 125d. The proximal end may include a spring 126 to enable inner drive shaft 125 to move forward and backward in the longitudinal direction within central-sheath 130, for example. The proximal end may be configured to connect and disconnect with a powered driver, for example. The distal end 125d may include a drive portion 127 to securely couple to a head portion of a bone screw 112, for example. In various embodiments, inner-shaft 125 may rotate clockwise and/or counter clockwise within central-sheath 130 and outer-sheath 120, for example. For example still, inner-shaft 125 may rotate clockwise and counterclockwise around the longitudinal axis defined by outer-sheath 120. Additionally, in various embodiments, outer-sheath 120 may be configured to house the same, similar, or substantially the same instrument as the various surgical instruments disclosed in U.S. patent application Ser. No. 16/560,587, and U.S. patent application Ser. No. 16/395,574, the disclosure of each is incorporated herein in entirety. For example, the various surgical systems, and tools may be inserted within the interior void space of outer-sheath 120 and utilized to drive a bone screw in the same, substantially the same, and/or similar manner as would be readily apparent to a person having ordinary skill in the art unless the arrangement of parts and context clearly indicates otherwise. Additionally, in some embodiments, central-sheath 130 and inner-shaft 125 may be referred to as a single instrument, for example a rotatable driver.

Figure 4:
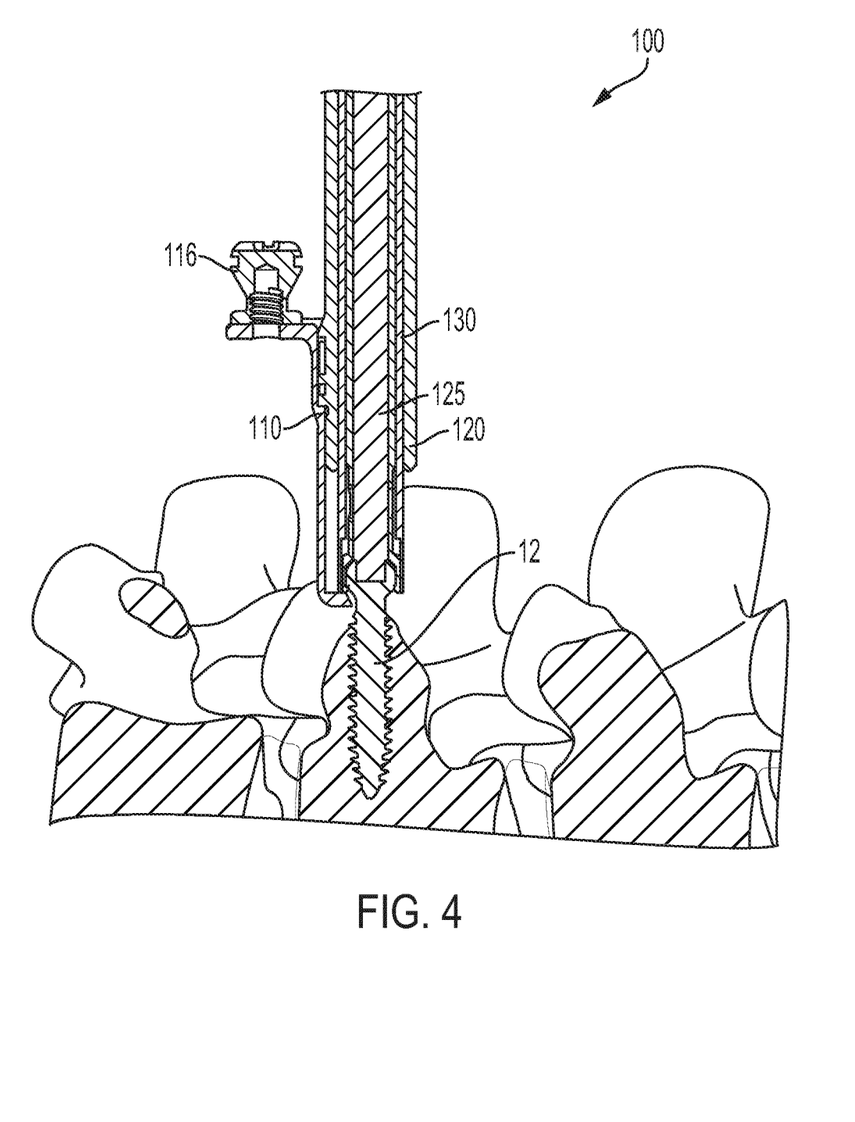
FIG. 4 is a cross section of the surgical tool of FIG. 1.

FIG. 4 is a cross section of a surgical tool 100 coupled to a blade 110 after driving a bone screw 12 within a vertebrae of a patient. In the example illustration, surgical tool 100 includes an outer-sheath 120 housing a central-sheath 130 that in turn houses an inner-shaft 125. For example, outer-sheath 120, central-sheath 130, and inner-shaft 125 are in a coaxial relationship where inner-shaft 125 may freely rotate within outer-sheath 120. Additionally, drive portion 127 of inner-shaft 125 may be coupled to bone screw 12 to facilitate rotation of bone screw 12 and the driving of bone screw 12 into the vertebrae of a patient, for example. Furthermore, blade 110 may be removably coupled to outer-sheath 120, for example via lower coupling portion 122. In this way, it is shown that surgical tool 100 may concurrently (simultaneously) install a bone screw 12 into a boney structure and deliver a blade 110 into the same vicinity for retaining patient tissue.

Figure 5:
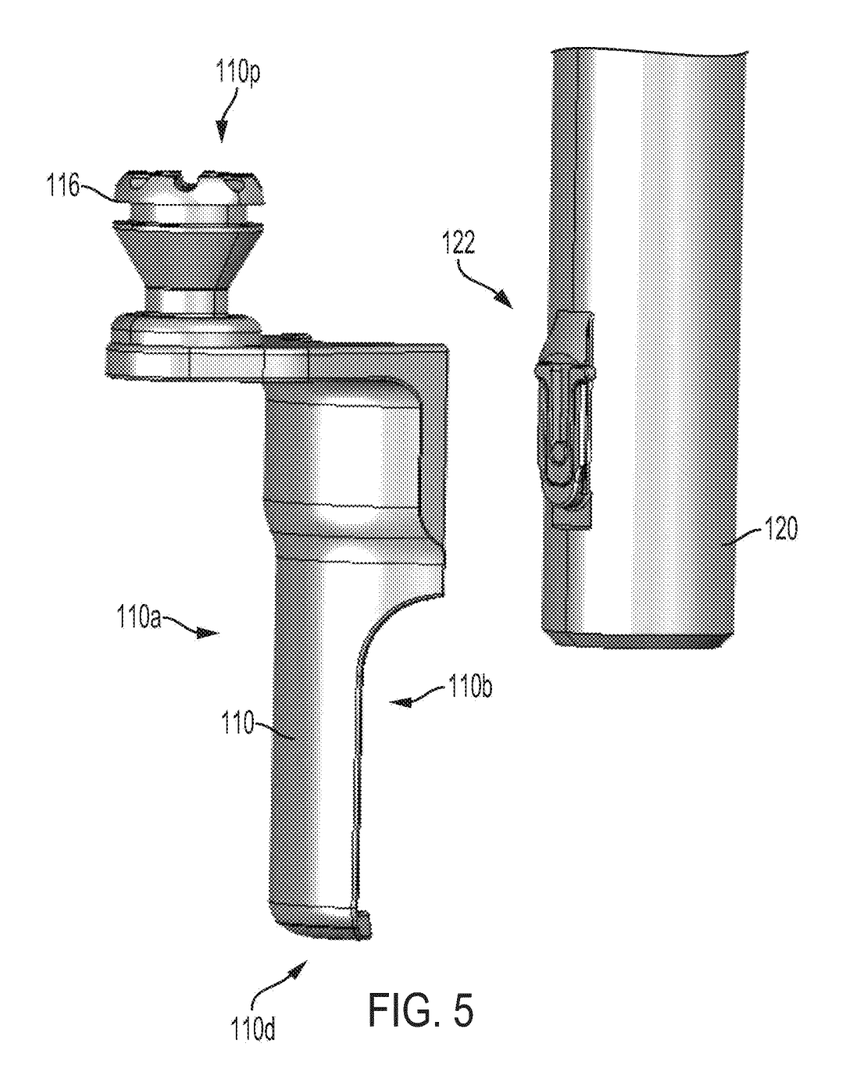
FIG. 5 is an enlarged perspective view of a portion of a surgical tool and a modular blade.
Figure 6:
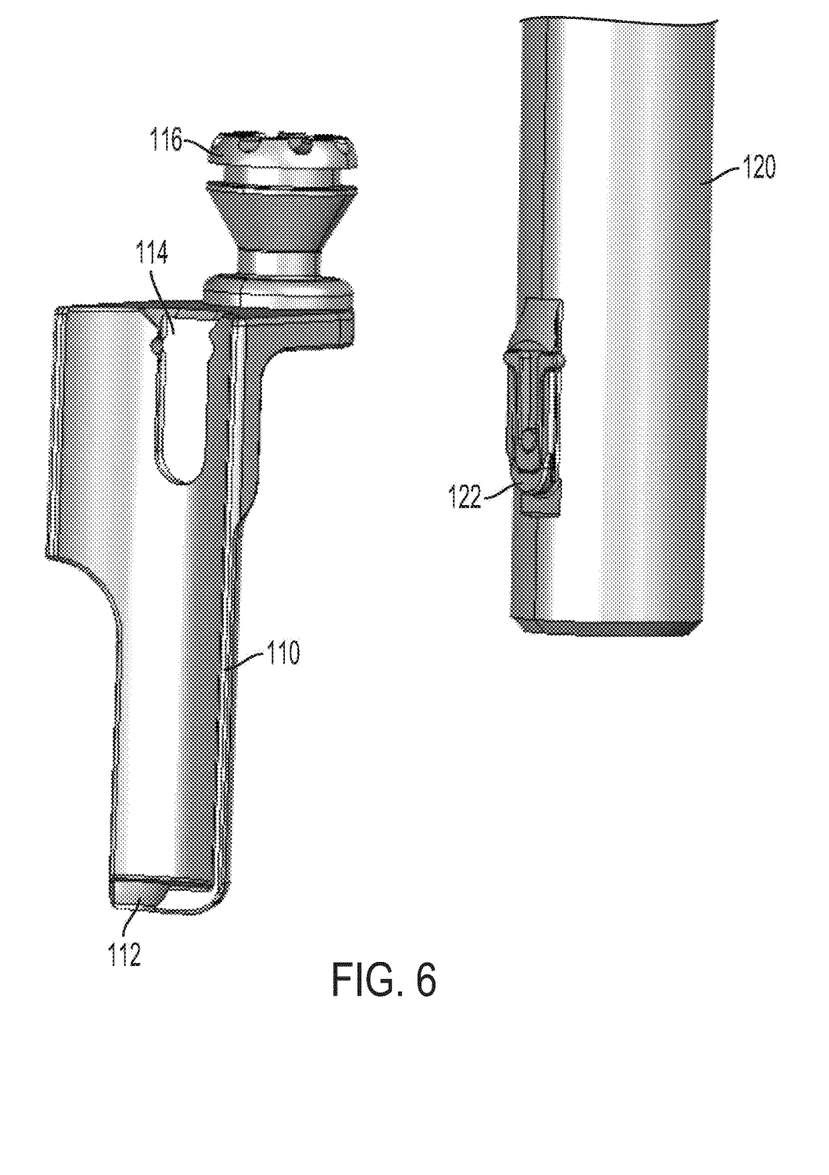
FIG. 6 is an alternate perspective view of a portion of a surgical tool and a modular blade.

FIG. 5 and FIG. 6 are enlarged perspective views of a portion of a surgical tool 100 and a modular blade 110. Modular blade 110 may extend from a proximal end 110p to a distal end 110d, for example. The proximal side 110p may include a fastener 116 for coupling blade 110 to a retractor 200, for example. As illustrated, modular blade 110 may include an exterior lateral sidewall 110a (tissue facing side 110a) and an interior lateral sidewall 110b (screw facing side 110b). In the illustrated embodiment, sidewalls 110a, 110b comprise a non-planar curved surface generally corresponding in size and shape to the outer diameter of outer-sheath 120. However, in other embodiments outer-sheath 120 may be alternately shaped, and blades 110 may be correspondingly shaped. For example, a pentagon shape, hexagon shape, rectangular shape, etc. In various embodiments, blade 110 may removably couple to outer-sheath 120 via coupling portion 122, for example. Referring to FIG. 6, it is shown that blade 110 may include a coupling channel 114 for securely attaching blade 110 to the coupling portion 122. Coupling channel 114 may comprise an indented portion and coupling portion 122 may comprise an outdented portion, at least with respect to their associated surfaces, for example.

In operation, an end user may move outer-sheath 120 and/or blade 110 such that coupling portion 122 may be slid into coupling channel 114, for example in a downward direction with respect to FIG. 6. The coupling portion 122 may nest within coupling channel 114. In various embodiments, the coupling portion 122 may disconnect from coupling channel 114 by lifting upward with sufficient force, i.e., coupling portion 122 and coupling channel 114 are attached by a connecting force that can be disassociated merely by pulling the outer-sheath 120 away from the blade 110 with a sufficient force to overcome the connecting force. For example still, the coupling channel 114 and coupling portion 122 may be connected by a spring loaded force or spring loaded tab comprising a biasing element and tabs. In other embodiments, a locking portion or actuator may secure blade 110 to outer-sheath 120 in similar manner as explained above. In those embodiments including a locking portion, an end user may first unlock the locking portion or actuator before disconnecting the surgical tool 100 from blade 110.

Figure 7A:
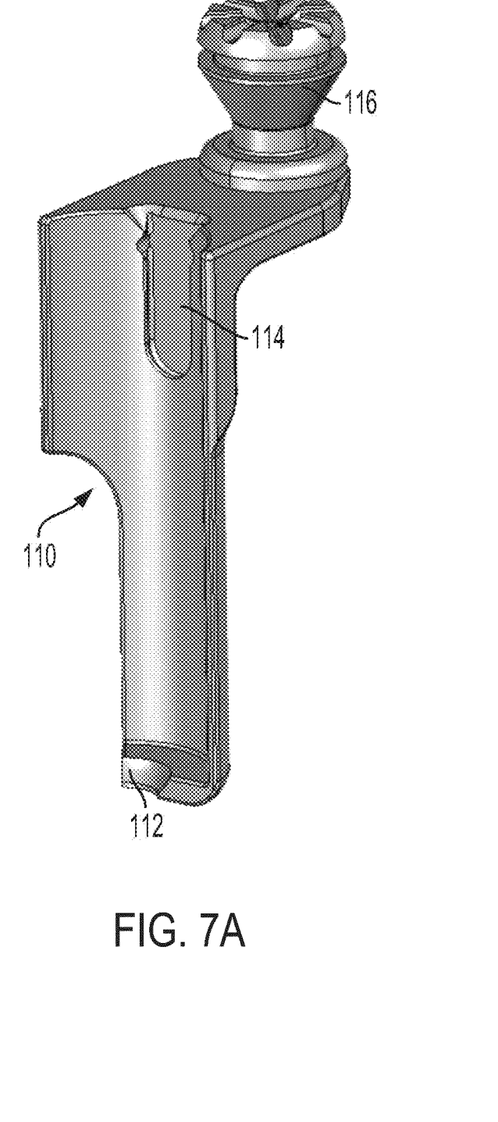
FIG. 7A is a perspective view of a blade for use with a surgical tool.
Figure 7B:
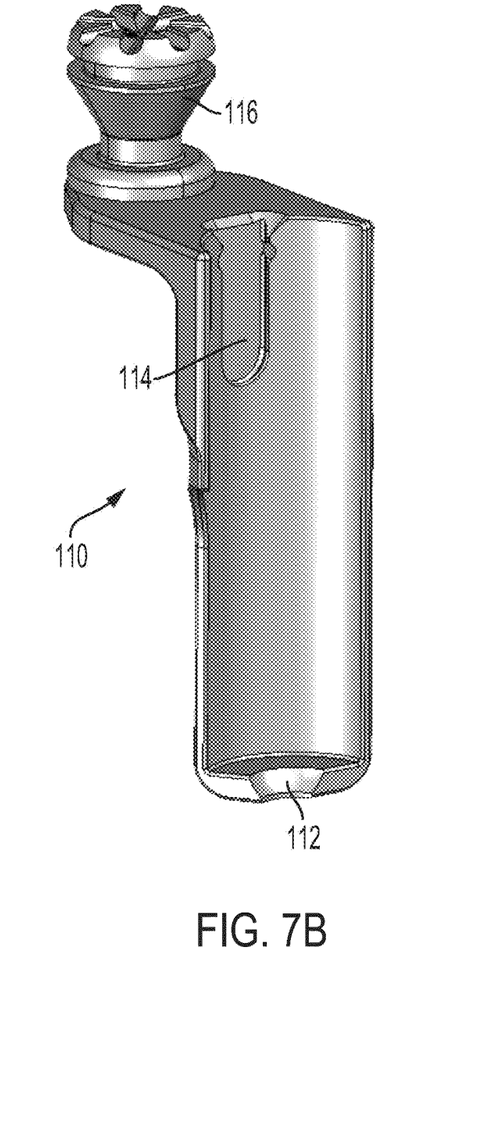
FIG. 7B is an alternate perspective view of a blade for use with a surgical tool.

FIGS. 7A and 7B are perspective views of a blade 110 for use with a surgical tool 100 as disclosed herein. Blade 110 may include a screw receiving portion 112, for example. In the example embodiment, screw receiving portion 112 may comprise an indented arcuate channel disposed at a distal end 110d of blade 110 for example. In other embodiments, screw receiving portion 112 may be alternately shaped depending on the head portion of bone screw 12, for example. In the disclosed embodiment, screw receiving portion 112 may be configured to surround a portion of the head of a bone screw 112, for example. The screw receiving portion 112 may have a size, shape, and general geometry that corresponds to the size, shape, and general geometry of the head portion of bone screw 12. For example, approximately 15%-50% of the underside of the head of bone screw 12 may nest within an arcuate and sloped surface of screw receiving portion 112. In at least one embodiment, screw receiving portion 112 is configured to rotatably support about 25% of the bottom half surface of a head of a bone screw 12 and bone screw 12 may have a generally dome shaped head portion. It shall be understand that the dome shaped head portion as immediately described may be understand as being severable into a top half and a bottom half. For example, the head portion of a bone screw 12 may include a top dome surface and a bottom dome surface. The bottom dome surface may adjoin a threaded portion there below. The head portion of the bone screw 12 may also include a planar side surface portion in some embodiments. Those with skill in the art will appreciate that the precise size, geometry, and structural attributes of screw receiving portion 112 may be designed in view of the particular size, geometry, and structural attributes of the head portion of a bone screw 12 or other anchoring member, implant, tool, probe, or the like. For example, a bone screw having a hex shaped head, a hexalobular shaped head, a cylindrical shaped head, etc. may suggest an alternately and correspondingly shaped screw receiving portion 112.

Figure 8:
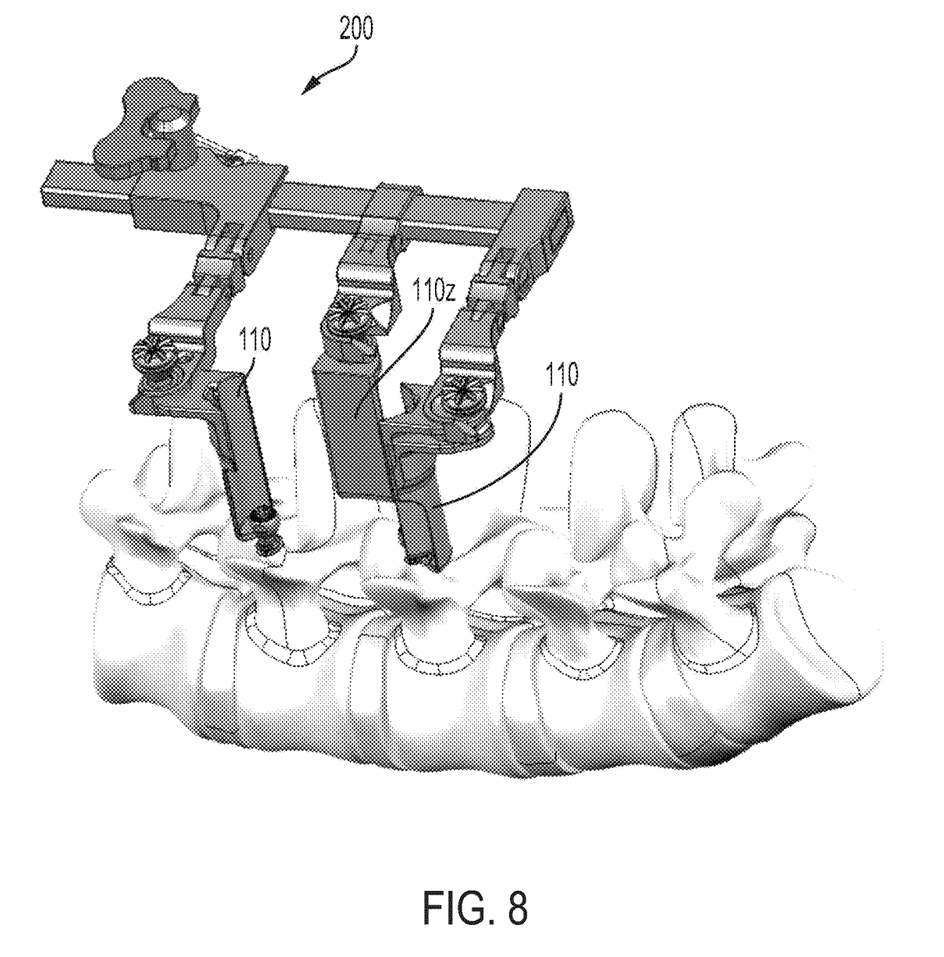
FIG. 8 is a perspective view of a retractor.
Figure 9:
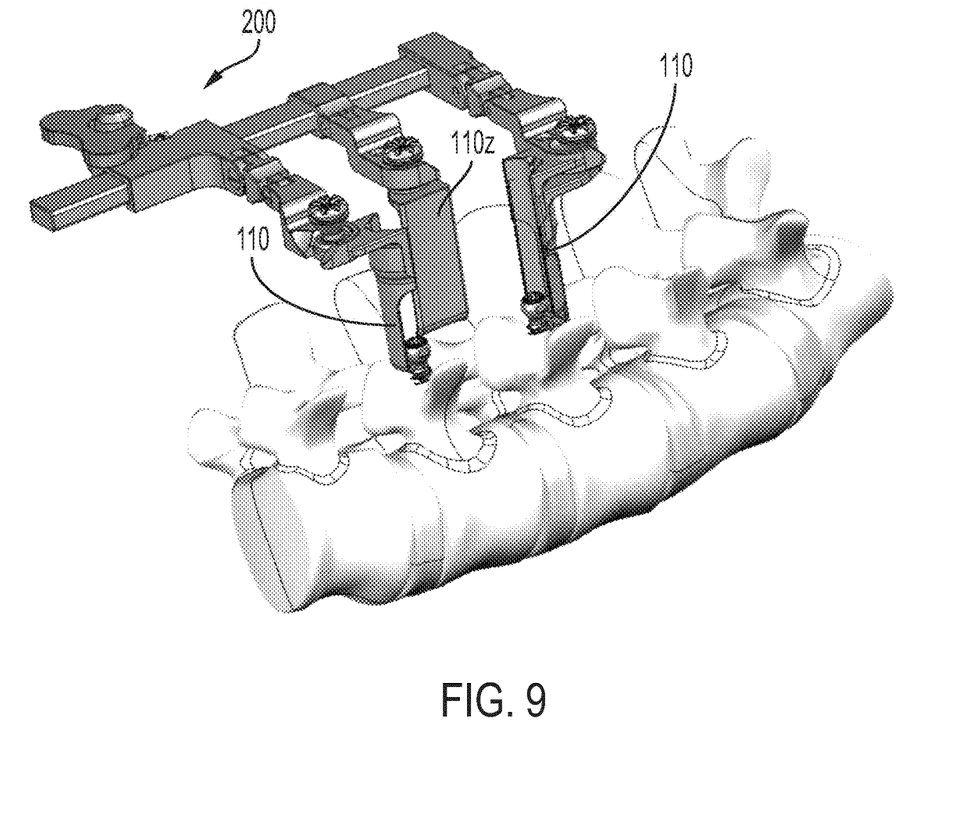
FIG. 9 is an alternate perspective view of the retractor of FIG. 8.

FIGS. 8 and 9 are example perspective views of an example retractor 200 including three blades 110, 110z. The example retractor 200 may include two modular blades 110 that each have or include a screw receiving portion 112 at a distal portion 110d similarly as described above, for example. Blades 110 may include a curved outer surface 110a and a curved inner surface 110b, for example. Distinct from blades 110, supplemental blade 110z may not include curved surfaces and/or a screw receiving portion 112. For example, supplemental blade 110z is substantially planar and is not configured for resting against a bone screw 12. However, in other embodiments, supplemental blade 110z may be configured in a similar manner as blades 110 and include a screw receiving portion 112 or the like with or without curved surfaces, for example.

In practice, an end user such as a surgeon may install blades 110 and bone screw 12 concurrently as described above. Next, the surgeon may secure retractor 200 to a table via a table mount. Next, the surgeon may position respective arms of retractor 200 adjacent a respective blade 110 while surgical tool 100 remains connected to blade 110, for example. Next, the surgeon may secure blades 110 to the respective arms of retractor 200 via fastener 116, for example. Next, the surgeon may uncouple each surgical tool 100 from each respective blade 110. For example, the surgeon may move surgical tool 100 upward and away from bone screw 12 with sufficient force to overcome the connection force between 114 and 122. It shall be understood that retractor 200 may be secured to a table (not illustrated) such that the relative position of blades 110 may not change and the force required to uncouple surgical tool 100 from blades 110 may be overcome with relative ease due to the table anchoring the retractor 200 in place.

Figure 10:
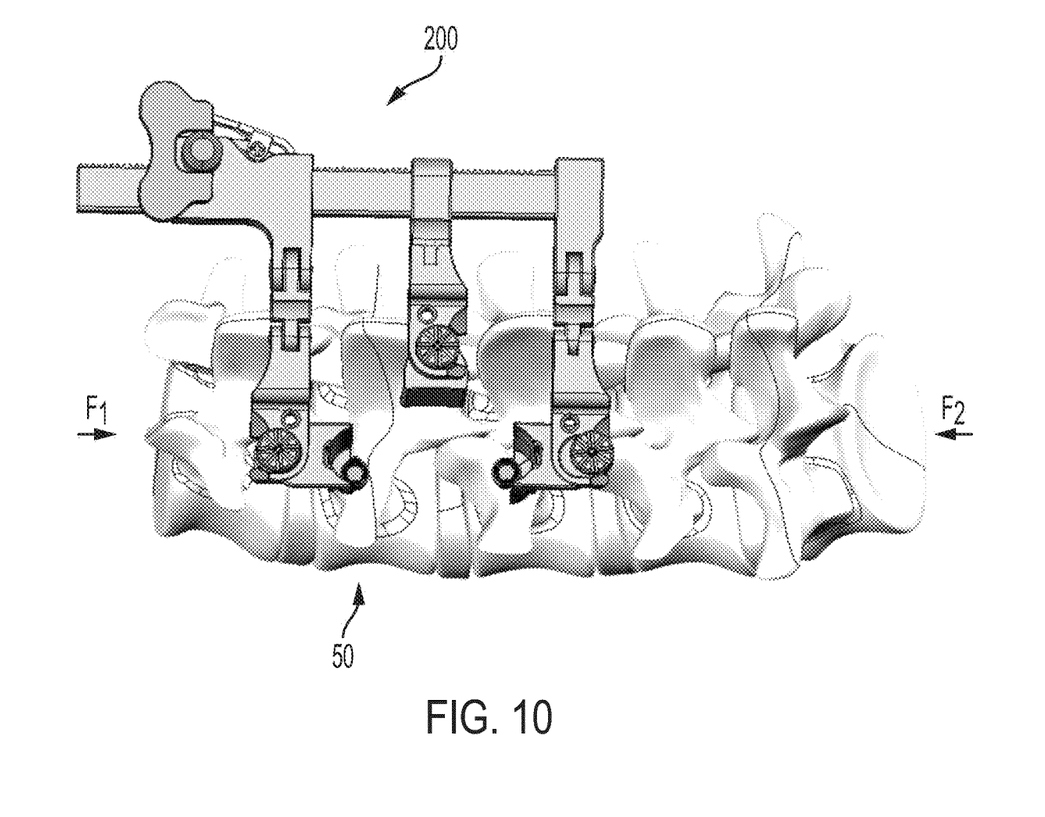
FIG. 10 is a top down view of the retractor of FIGS. 8 and 9.

FIG. 10 is an example top down view of a retractor 200 including two blades 110 and a supplemental blade 110z. As illustrated, blades 110, 110z define a surgical opening 50, for example. The retractor 200 may securely position the proximal end 110p of blades 110 such that blades 110 are restrained from moving upward, downward, and side to side, for example. Additionally, due to a head of bone screw 12 directly contacting and/or being nested within the screw receiving portion 112, blades 110 may act against bone screw 12 at a distal end 110d. For example, a force of a patients tissue (schematically shown via arrow $F_1$ and arrow $F_2$) may act against blades 110 pushing them towards a center of surgical opening 50 and the distal end 110d may remain in place relative to bone screw 12. For example still, head portion 12 may provide a fixed fulcrum point resisting the tendency for the distal end 110d of blades 110 to pivot inwards towards a center of surgical opening 50. In this way, an inward articulation of blades 110 may be suppressed and/or prevented.

Figure 11:
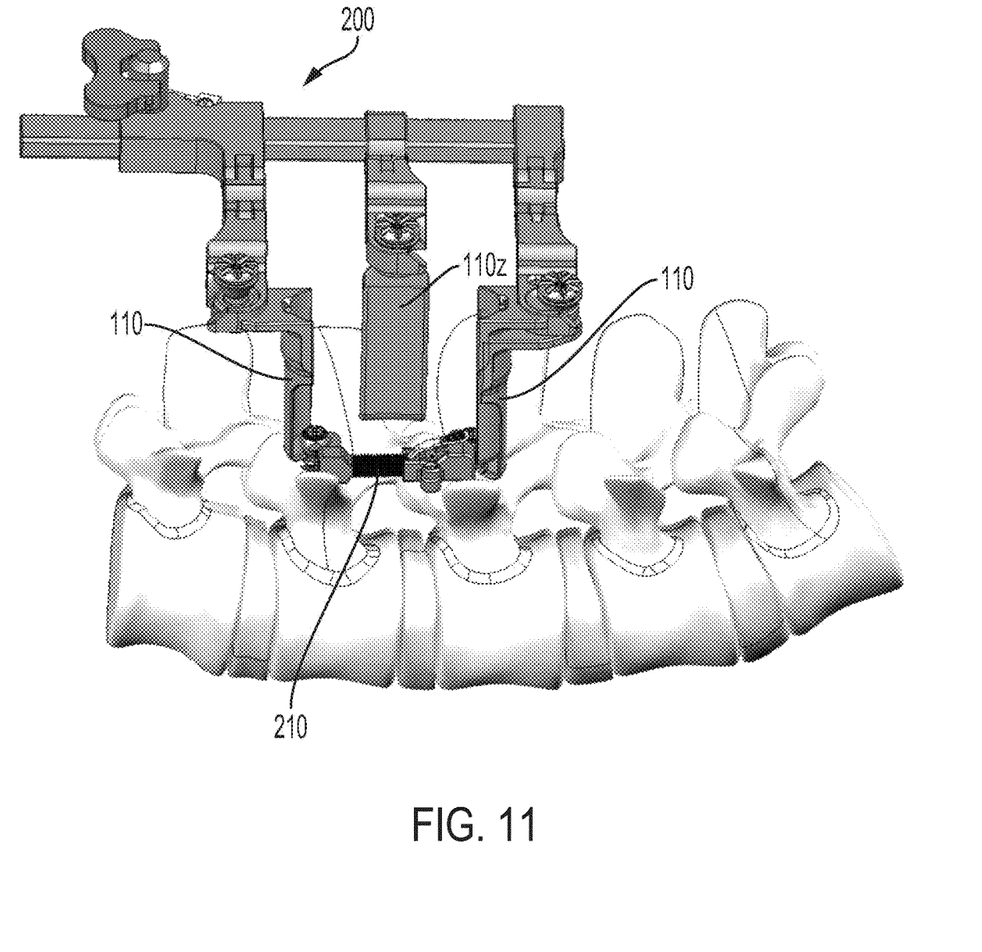
FIG. 11 is a perspective view of a retractor and an extension member.

FIG. 11 is a perspective view of a retractor 200 and an internal brace 210. Internal brace 210 may be positioned between bone screws 12 and mobile blades 110 such that it acts against bone screws 12 and/or mobile blades 110. The internal brace 210 may be utilized to suppress and/or prevent inward shrinkage of surgical opening 50 due to, for example, inward pressure from a patient's tissue such as forces $F_1$ and $F_2$. Additionally, internal brace 210 may be expanded to actively apply pressure against bone screws 12 and/or blades 110, for example. In various embodiments, retractor 200 may be the same as the modular surgical instrument system described in U.S. patent application Ser. No. 17/166,265, the entire disclosure of which is incorporated herein by reference in its entirety. For example, the surgical tool 100 and corresponding blades 110 of the present application may be used with the modular surgical instrument system of U.S. patent application Ser. No. 17/166,265 as would be readily apparent to a person having ordinary skill in the art.

It should be understood that various aspects disclosed herein may be combined in different combinations than the combinations specifically presented in the description and accompanying drawings. For example, features, functionality, and components from one embodiment may be combined with another embodiment and vice versa unless the context clearly indicates otherwise. Similarly, features, functionality, and components may be omitted unless the context clearly indicates otherwise. It should also be understood that, depending on the example, certain acts or events of any of the processes or methods described herein may be performed in a different sequence, may be added, merged, or left out altogether (e.g., all described acts or events may not be necessary to carry out the techniques).

Unless otherwise specifically defined herein, all terms are to be given their broadest possible interpretation including meanings implied from the specification as well as meanings understood by those skilled in the art and/or as defined in dictionaries, treatises, etc. It must also be noted that, as used in the specification and the appended claims, the singular forms "a," "an" and "the" include plural referents unless otherwise specified, and that the terms "comprises" and/or "comprising," when used in this specification, specify the presence of stated features, elements, and/or components, but do not preclude the presence or addition of one or more other features, steps, operations, elements, components, and/or groups thereof.

What is claimed is:

1. A surgical instrument, comprising:
    an elongated outer-sheath extending in a longitudinal direction from a proximal end to a distal end, the elongated outer-sheath having an interior cavity defining a centrally disposed longitudinal axis extending in the longitudinal direction; the elongated outer-sheath having a coupling rail disposed proximate to the distal end;
    a blade configured to couple to and uncouple from the elongated outer-sheath via the coupling rail, wherein a distal end of the blade comprises an indented arcuate channel configured to rotatably support about 15% to about 50% of an underside of a head portion of a bone screw;
    a central-sheath disposed within the interior cavity and extending in the longitudinal direction; and
    an inner-shaft rotatably supported by the central-sheath and extending in the longitudinal direction, the inner-shaft including a driver disposed proximate the distal end, the inner-shaft being rotatable about the longitudinal axis, wherein the surgical instrument is configured to enable simultaneously driving the bone screw into a boney structure of a patient in an installed position and delivery of the blade within the patient adjacent the installed position.

2. The surgical instrument of claim 1, wherein:
the elongated outer-sheath comprises a generally cylindrical shape having an outer surface, and
the blade comprises an interior side surface that corresponds in size and shape to the outer surface of the elongated outer-sheath.

3. The surgical instrument of claim 1, wherein:
the blade comprises a coupling channel disposed at a proximal end of the blade that is indented with respect to an interior surface of the blade,
the coupling rail of the elongated outer-sheath is outdented with respect to an outer surface of the outer-sheath, and
the coupling rail is slidably connected with the coupling channel.

4. The surgical instrument of claim 3, wherein the blade extends from the coupling rail of the elongated outer-sheath such that a distal end of the blade extends distally farther than the distal end of the elongated outer-sheath.

5. The surgical instrument of claim 1, wherein:
the arcuate channel of the bone screw receiving portion is sloped with respect to the longitudinal direction and directly contacts a bottom dome shaped surface of the head portion of the bone screw while the bone screw is being driven due to rotation of the inner shaft about the longitudinal axis, and
when the bone screw is being driven, the bottom dome shaped surface is partially nested with the arcuate channel.

6. The surgical instrument of claim 5, wherein the blade comprises a fastener disposed at a proximal end of the blade for coupling to a retractor.

7. The surgical instrument of claim 1, wherein the central-sheath includes an enlarged proximal end extending proximally farther than the proximal end of the elongated outer-sheath and having a cross sectional width that is greater than an average cross sectional width of the elongated outer-sheath.

8. The surgical instrument of claim 7, wherein:
a proximal end of the inner shaft extends into the enlarged proximal end of the central sheath,
the enlarged proximal end of the central sheath comprises a spring that biases the inner-shaft towards the distal end of the elongated outer-sheath, and
the inner-shaft is movable forward and backward in the longitudinal direction.

9. The surgical instrument of claim 8, wherein the inner-shaft includes an end portion connectable to a powered drive instrument, the end portion extending proximally farther than the proximal end of the elongated outer-sheath.

10. A surgical system, comprising:
a blade including an indented arcuate channel at a distal end thereof;
a bone screw having a spherical head comprising an upper dome shaped surface and a lower dome shaped surface; and
a surgical instrument configured to enable simultaneously driving the bone screw into a boney structure of a patient in an installed position and delivering the blade within the patient adjacent the installed position, wherein the surgical instrument comprises:
an elongated outer-sheath extending in a longitudinal direction from a proximal end to a distal end, the elongated outer-sheath having an interior cavity defining a centrally disposed longitudinal axis extending in the longitudinal direction, the elongated outer-sheath having a coupling rail disposed proximate to the distal end; and
a rotatable driver disposed within the interior cavity and extending in the longitudinal direction and rotatable about the longitudinal axis, wherein the blade is configured to selectively couple to and uncouple from the elongated outer-sheath; and
wherein the indented arcuate channel is configured to directly contact about 15% to about 50% of the lower dome shaped surface of the bone screw while the surgical instrument drives the bone screw into the boney structure of the patient.

11. The surgical system of claim 10, wherein:
the elongated outer-sheath comprises a generally cylindrical shape having an outer surface, and
the blade comprises an interior side surface that corresponds in size and shape to the outer surface of the elongated outer-sheath.

12. The surgical instrument of claim 10, wherein the blade extends in the longitudinal direction and the indented arcuate channel is sloped with respect to the longitudinal direction.

13. The surgical instrument of claim 12, wherein the indented arcuate channel of the bone screw receiving portion is configured to rotatably support the bone screw such that the lower dome shaped surface of the bone screw slides across the indented arcuate channel when the bone screw is being driven by the rotatable driver.

14. The surgical instrument of claim 10, further comprising a retractor, and
wherein the blade comprises a fastener disposed at a proximal end of the blade, the fastener being configured to selectively couple to the retractor.

15. A method for simultaneously delivering a blade and a bone screw, comprising:
providing a surgical instrument comprising:
an elongated outer-sheath extending in a longitudinal direction from a proximal end to a distal end, the elongated outer-sheath having an interior cavity defining a centrally disposed longitudinal axis extending in the longitudinal direction; the elongated outer-sheath having a coupling rail disposed proximate to the distal end;
a central-sheath disposed within the interior cavity and extending in the longitudinal direction; and
an inner-shaft rotatably supported by the central-sheath and extending in the longitudinal direction, the inner-shaft including a driver disposed proximate the distal end;
providing a blade comprising a bone screw receiving portion, the bone screw receiving portion comprises an indented arcuate channel;
coupling the blade to the elongated outer-sheath via the coupling rail;
providing a bone screw having a head portion including a lower dome shaped surface generally corresponding in size and shape to the bone screw receiving portion;
coupling the bone screw to the driver;

supporting about 15% to about 50% of the lower dome shaped surface of the bone screw with the indented arcuate channel;

installing, simultaneously, the bone screw in a boney structure of a patient in an installed position and the blade in the patient, wherein the bone screw is installed by rotating the driver such that the lower dome shaped surface of the bone screw slides across the indented arcuate channel.

16. The method of claim 15, wherein:

the indented arcuate channel is sloped with respect to the longitudinal direction, and when the bone screw is in the installed position a bottom surface of a head portion of the bone screw directly contacts the indented arcuate channel.

17. The method of claim 16, comprising:

positioning an arm of a retractor adjacent the installed bone screw and blade; and coupling a fastener of the blade to the arm of the retractor; and uncoupling, after completing the coupling the fastener step, the blade from the outer-sheath.

\* \* \* \* \*